US008109919B2

(12) United States Patent
Kraft et al.

(10) Patent No.: US 8,109,919 B2
(45) Date of Patent: *Feb. 7, 2012

(54) DEVICE AND METHOD FOR RAPID ASPIRATION AND COLLECTION OF BODY TISSUE FROM WITHIN AN ENCLOSED BODY SPACE

(76) Inventors: Daniel Kraft, Stanford, CA (US); James Hole, Burlingame, CA (US)

( * ) Notice: Subject to any disclaimer, the term of this patent is extended or adjusted under 35 U.S.C. 154(b) by 1345 days.

This patent is subject to a terminal disclaimer.

(21) Appl. No.: 11/675,031

(22) Filed: Feb. 14, 2007

(65) Prior Publication Data

US 2007/0154460 A1 Jul. 5, 2007

Related U.S. Application Data

(63) Continuation of application No. 10/454,846, filed on Jun. 4, 2003, now Pat. No. 7,462,181.

(60) Provisional application No. 60/384,998, filed on Jun. 4, 2002.

(51) Int. Cl.
*A61M 31/00* (2006.01)
*A61M 1/00* (2006.01)
*A61M 25/01* (2006.01)
(52) U.S. Cl. .......... 604/522; 604/35; 604/239; 604/500
(58) Field of Classification Search .................. 433/165, 433/166; 600/562, 564–568; 604/35, 239, 604/500, 522; 606/79, 86 R, 167, 170, 180
See application file for complete search history.

(56) References Cited

U.S. PATENT DOCUMENTS

| | | |
|---|---|---|
| 4,116,066 A | 9/1978 | Mehl et al. |
| 4,142,517 A | 3/1979 | Stavropoulos et al. |
| 4,407,294 A | 10/1983 | Vilkomerson |
| 4,513,754 A | 4/1985 | Lee |
| 4,747,414 A | 5/1988 | Brossel |
| 5,014,715 A | 5/1991 | Chapolini |
| 5,257,632 A | 11/1993 | Turkel et al. |
| 5,269,785 A | 12/1993 | Bonutti |

(Continued)

FOREIGN PATENT DOCUMENTS

CA 2495962 A1 3/2004

(Continued)

OTHER PUBLICATIONS

European Patent Application No. 03731524.9 filed Jun. 4, 2003 in the name of Kraft et al., Office Action mailed Apr. 23, 2009.

(Continued)

*Primary Examiner* — Max Hindenburg
*Assistant Examiner* — Emily Lloyd
(74) *Attorney, Agent, or Firm* — Levine Bagade Han LLP

(57) ABSTRACT

Device and method for rapid extraction of body tissue from an enclosed body cavity. Hollow entry cannula with optional core element provides entry into body tissue space such as bone marrow. Aspiration cannula is inserted through cannula into body tissue and is manipulated to advance directionally through body cavity. Optional stylet within aspiration cannula aids in advancing aspiration cannula through body tissue and is removed to facilitate extraction of body tissue through the aspiration cannula. Inlet openings near distal tip of aspiration cannula allow tissue aspiration, with negative pressure source at proximal end of aspiration cannula providing controlled negative pressure. Aspiration cannula may be withdrawn and its path adjusted for multiple entries through the same entry point, following different paths through tissue space for subsequent aspiration of more tissue.

25 Claims, 16 Drawing Sheets

U.S. PATENT DOCUMENTS

| | | | |
|---|---|---|---|
| 5,285,795 A | 2/1994 | Ryan et al. |
| 5,306,278 A | 4/1994 | Dahl et al. |
| 5,324,300 A | 6/1994 | Elias et al. |
| 5,357,974 A | 10/1994 | Baldridge |
| 5,429,638 A | 7/1995 | Muschler et al. |
| 5,456,267 A | 10/1995 | Stark |
| 5,486,161 A | 1/1996 | Lax et al. |
| 5,488,958 A | 2/1996 | Topel et al. |
| 5,571,085 A | 11/1996 | Accisano, III |
| 5,626,579 A | 5/1997 | Muschler et al. |
| 5,668,288 A | 9/1997 | Storey et al. |
| 5,824,084 A | 10/1998 | Muschler |
| 5,913,859 A | 6/1999 | Shapira |
| 5,954,671 A | 9/1999 | O'Neill |
| 6,018,094 A | 1/2000 | Fox |
| 6,049,026 A | 4/2000 | Muschler |
| 6,063,037 A | 5/2000 | Mittermeier et al. |
| 6,110,176 A | 8/2000 | Shapira |
| 6,159,163 A | 12/2000 | Strauss et al. |
| 6,264,618 B1 | 6/2001 | Landi et al. |
| 6,306,575 B1 | 10/2001 | Thomas et al. |
| 6,315,737 B1 | 11/2001 | Skinner |
| 6,325,806 B1 | 12/2001 | Fox |
| 6,328,765 B1 | 12/2001 | Hardwick et al. |
| 6,358,252 B1 | 3/2002 | Shapira |
| 6,425,887 B1 | 7/2002 | McGuckin et al. |
| 6,432,653 B1 | 8/2002 | Okarma |
| 6,440,138 B1 | 8/2002 | Reiley et al. |
| 6,488,636 B2 | 12/2002 | Bryan et al. |
| 6,537,290 B2 | 3/2003 | Adams et al. |
| 6,543,455 B2 | 4/2003 | Bonutti |
| 6,755,793 B2 | 6/2004 | Lamoureux et al. |
| 6,846,314 B2 | 1/2005 | Shapira |
| 6,849,051 B2 | 2/2005 | Sramek et al. |
| 6,902,559 B2 | 6/2005 | Taufig |
| 6,913,463 B2 | 7/2005 | Blacklock |
| 6,916,292 B2 | 7/2005 | Morawski et al. |
| 6,981,948 B2 | 1/2006 | Pellegrino et al. |
| 7,081,123 B2 | 7/2006 | Merboth et al. |
| 7,462,181 B2 | 12/2008 | Kraft et al. |
| 7,488,322 B2 | 2/2009 | Brunnett et al. |
| 2002/0042581 A1 | 4/2002 | Cervi |
| 2002/0055755 A1 | 5/2002 | Bonutti |
| 2002/0058945 A1 | 5/2002 | Steiner et al. |
| 2002/0085996 A1 | 7/2002 | McIntosh et al. |
| 2002/0107531 A1 | 8/2002 | Schreck et al. |
| 2002/0128602 A1 | 9/2002 | Adams et al. |
| 2002/0138021 A1 | 9/2002 | Pflueger |
| 2002/0161449 A1 | 10/2002 | Muschler |
| 2002/0165600 A1 | 11/2002 | Banas et al. |
| 2003/0055373 A1 | 3/2003 | Sramek et al. |
| 2003/0078586 A1 | 4/2003 | Shapira |
| 2003/0205029 A1 | 11/2003 | Chapolini |
| 2003/0208181 A1 | 11/2003 | Geise et al. |
| 2003/0225344 A1 | 12/2003 | Miller |
| 2003/0225364 A1 | 12/2003 | Kraft et al. |
| 2003/0225411 A1 | 12/2003 | Miller |
| 2004/0191897 A1 | 9/2004 | Muschler |
| 2005/0171504 A1 | 8/2005 | Miller |
| 2006/0052790 A1 | 3/2006 | Miller |
| 2006/0229624 A1 | 10/2006 | May et al. |
| 2006/0247552 A1 | 11/2006 | Ikehara et al. |
| 2007/0016100 A1 | 1/2007 | Miller |
| 2007/0055282 A1 | 3/2007 | Muschler |
| 2007/0135759 A1 | 6/2007 | Kraft et al. |
| 2007/0197996 A1 | 8/2007 | Kraft et al. |

FOREIGN PATENT DOCUMENTS

| | | |
|---|---|---|
| EP | 1175866 B1 | 12/2006 |
| JP | 61-106210 | 5/1986 |
| JP | 08019618 A | 1/1996 |
| JP | 11128237 A | 5/1999 |
| JP | 2001-079013 | 3/2001 |
| JP | 2002-513608 | 5/2002 |
| WO | WO99/56628 A1 | 11/1999 |
| WO | WO 01/22889 | 4/2001 |
| WO | WO 01/78590 | 10/2001 |
| WO | WO 03/013336 A2 | 2/2003 |
| WO | WO 03/057045 A1 | 7/2003 |
| WO | WO 03/101308 | 12/2003 |
| WO | WO2004/090111 A2 | 10/2004 |
| WO | WO2005/046769 A2 | 5/2005 |
| WO | WO2007/018809 A2 | 2/2007 |
| WO | WO2008/002961 A2 | 1/2008 |
| WO | WO2008/016757 A2 | 2/2008 |
| WO | WO 2008/033871 A2 | 3/2008 |
| WO | WO2008/033874 A2 | 3/2008 |
| WO | WO2008/054894 A2 | 5/2008 |

OTHER PUBLICATIONS

Japanese Patent Application No. 2004-508671 filed Jun. 4, 2003 in the name of Kraft et al., Office Action mailed Apr. 7, 2009.

Japanese Patent Application No. 2004-508671 filed Jun. 4, 2003 in the name of Kraft et al., Office Action mailed Dec. 22, 2009.

Japanese Patent Application No. 2004-508671 filed Jun. 4, 2003 in the name of Kraft et al., Office Action mailed Aug. 10, 2010.

PCT International Application No. PCT/US2003/017511 filed Jun. 4, 2003 in the name of Kraft et al., International Search Report and Written Opinion mailed Oct. 29, 2003.

U.S. Appl. No. 10/454,846, filed Jun. 4, 2003 in the name of Kraft et al., Examiner's Amendment mailed Aug. 15, 2008.

U.S. Appl. No. 10/454,846, filed Jun. 4, 2003 in the name of Kraft et al., Final Office Action mailed Apr. 29, 2008.

U.S. Appl. No. 10/454,846, filed Jun. 4, 2003 in the name of Kraft et al., Non-Final Office Action mailed Oct. 4, 2007.

U.S. Appl. No. 10/454,846, filed Jun. 4, 2003 in the name of Kraft et al., Notice of Allowance mailed Aug. 15, 2008.

U.S. Appl. No. 10/454,846 filed Jun. 4, 2003 in the name of Kraft et al., Notice of Allowance mailed Oct. 6, 2008.

U.S. Appl. No. 11/675,019, filed Feb. 14, 2007 in the name of Kraft et al., Final Office Action mailed Apr. 28, 2008.

U.S. Appl. No. 11/675,019, filed Feb. 14, 2007 in the name of Kraft et al., Final Office Action mailed Apr. 9, 2009.

U.S. Appl. No. 11/675,019, filed Feb. 14, 2007 in the name of Kraft et al., Final Office Action mailed Oct. 6, 2009.

U.S. Appl. No. 11/675,019, filed Feb. 14, 2007 in the name of Kraft et al., Non-final Office Action mailed Aug. 5, 2008.

U.S. Appl. No. 11/675,019, filed Feb. 14, 2007 in the name of Kraft et al., Non-final Office Action mailed Jun. 23, 2010.

U.S. Appl. No. 11/675,019, filed Feb. 14, 2007 in the name of Kraft et al., Non-final Office Action mailed Oct. 5, 2007.

U.S. Appl. No. 11/675,035, filed Feb. 14, 2007 in the name of Kraft et al., Final Office Action mailed Apr. 29, 2010.

U.S. Appl. No. 11/675,035, filed Feb. 14, 2007 in the name of Kraft et al., Non-final Office Action mailed Oct. 12, 2007.

U.S. Appl. No. 11/675,035, filed Feb. 14, 2007 in the name of Kraft et al., Non-final Office Action mailed May 13, 2008.

U.S. Appl. No. 11/675,035, filed Feb. 14, 2007 in the name of Kraft et al., Final Office Action mailed Nov. 10, 2008.

U.S. Appl. No. 11/675,035, filed Feb. 14, 2007 in the name of Kraft et al., Non-final Office Action mailed Jul. 22, 2009.

U.S. Appl. No. 11/675,035, filed Feb. 14, 2007 in the name of Kraft et al., Advisory Action mailed Jun. 17, 2010.

Ohashi, K. et. al., "Stem Cell Harvesting Device with Passive Flexible Drilling Unit for Bone Marrow Transplantation," *IEEE Transactions on Robotics and Automation*, vol. 19, No. 5, p. 810-817, Oct. 2003.

Ohashi, K. et al., "Development of Minimally Invasive Bone Marrow Cell Harvester," Abstracts of the Convention of the Japanese Society of Computer-Aided Surgery, Nov. 2001; p. 101; Certification of Translation and Translation p. 1-4.

Ohashi, K. et al., "Development of a Minimally Invasive Bone Marrow Cell Harvester for Bone Marrow Transplantation," Minutes and Papers Presented at the 41st Convention of the Japanese Society of Medical Electronics and Biological Engineering, May 9-11, 2002; p. 66, Certification of Translation and Translation p. 1-3.

Ohashi, K. et al., "A Stem Cell Harvesting Manipulator with Flexible Drilling Unit for Bone Marrow Transplantation," Proc. of the 5th International Conference on Medical Image Computing and Computer Assisted Intervention (MICCAI '02), Sep. 25-28, 2002; p. 192-199, vol. 1 (2002).

Ohashi, K. et al., "A Manipulator with Flexible Drilling Unit for Hematopoietic Stem Cell Harvesting," Proc. of the Second Joint Meeting of the IEEE Engineering in Medicine and Biology Society (EMBS 2002), Oct. 23-26, 2002; p. 689-690 (CD-ROM).

Ohashi, K. et al., "Stem Cell Harvesting Device with Passive Flexible Drilling Unit for Bone Marrow Transplantation," IEEE Transactions on Robotics and Automation, Oct. 2003, p. 810-817, vol. 19, No. 5.

U.S. Appl. No. 11/675,019, filed Feb. 14, 2007 in the name of Kraft et al., Notice of Allowance mailed May 26, 2011.

U.S. Appl. No. 11/675,019, filed Feb. 14, 2007 in the name of Kraft et al., Notice of Allowance mailed Jun. 6, 2011.

DEVICE AND METHOD FOR RAPID ASPIRATION AND COLLECTION OF BODY TISSUE FROM WITHIN AN ENCLOSED BODY SPACE

CROSS-REFERENCE TO RELATED APPLICATIONS

This application is a continuation of U.S. application Ser. No. 10/454,846 filed Jun. 04, 2003 which claims priority to U.S. Provisional Application No. 60/384,998 filed Jun. 04, 2002, each of which is incorporated herein by reference in its entirety.

BACKGROUND

1. Field

Invention relates generally to the field of medicine and more specifically to a device and method for rapid extraction of tissue from an enclosed body cavity.

2. Related Art

Bone Marrow is a rich source of pluripotent hematopoietic stem cells from which red blood cells, white blood cells, and platelets are formed. Bone marrow also contains additional populations of cells which have the potential to regenerate other tissues.

Since the early 1970's bone marrow and hematopoietic stem cell transplantation has been used to treat patients with a wide variety of disorders, including but not limited to cancer, genetic and autoimmune diseases. Currently over 400,000 transplants for a variety of indications are performed worldwide each year.

In autologous transplants, the patient has their own bone marrow collected prior to receiving high dose chemotherapy. Following high dose, myeloablative chemotherapy (which kills the majority of the patients marrow stem cells) the stored autologous marrow (or hematopoietic stem cells purified or enriched from the marrow) is infused, and serves to 'rescue' the patient's hematolymphoid system.

In allogeneic transplants bone marrow, or other sources of hematopoietic stem cells derived from a full or partially human leukocyte antigen (HLA) matched sibling, parent or unrelated donor is infused into the recipient patient and following engraftment, serves to reconstitute the recipients hematopoietic system with cells derived from the donor.

Following myeloablative or non-myeloablative conditioning of a patient with chemotherapy and/or radiation therapy, the marrow is regenerated through the administration and engraftment of hematopoietic stem cells contained in the donor bone marrow.

In addition to hematopoietic stem cells and hematopoietic progenitors, bone marrow contains mesenchymal and other stem cell populations thought to have the ability to differentiate into muscle, myocardium, vasculature and neural tissues and possibly some organ tissues such as liver and pancreas. Recent research in preclinical animal studies (for example Rafii S, et al., Contribution of marrow-derived progenitors to vascular and cardiac regeneration, Semin Cell Dev Biol 2002 February; 13(1):61-7) and clinical trials (for example of recent clinical trials and methods see Strauer B E, Wernet P. et al. Repair of infracted myocardium by autologous intracoronary mononuclear bone marrow cell transplantation in humans. Circulation Oct. 8, 2002;106(15):1913-8, and the article by Stamm C, et al. Autologous bone-marrow stem-cell transplantation for myocardial regeneration. Lancet Jan. 4, 2003; 361 (9351):45-6) suggest that bone marrow or some portion of the cells contained within marrow can regenerate tissues other than the hematopoietic system. This includes the ability for cells contained within the marrow to regenerate or facilitate regeneration of myocardial tissue following a myocardial infarction, as evident by improved cardiac function and patient survival (Strauer B E, et al. Intracoronary, human autologous stem cell transplantation for myocardial regeneration following myocardial infarction, Dtsch Med Wochenschr Aug. 24, 2001; 126(34-35):932-8).

Bone marrow derived stem cells also show evidence for their ability to regenerate damaged liver and hepatic cells (Lagasse E et al Purified hematopoietic stem cells can differentiate into hepatocytes in vivo, Nature Medicine 2000 November; 6(11): 1229-34) and portions of the nervous system (Cuevas P et al. Peripheral nerve regeneration by bone marrow stromal cells, Neurol Res 2002 October;24(7):634-8 Arthritis Res Ther 2003;5(1):32A5) including spinal cord (Wu S et al Bone marrow stromal cells enhance differentiation of cocultured neurosphere cells and promote regeneration of injured spinal cord. J Neurosci Res 2003 May 1;72(3): 343-51.). Additional organ systems including kidney show benefit from bone marrow derived cells (Poulsom R et al. Bone marrow stem cells contribute to healing of the kidney, J Am Soc Nephrol 2003 June;14 (Suppl 1):S48-54). Use of bone marrow and the stem cells contained within bone marrow may be of increasing clinical utility in the future treatment of patients.

Stem cells utilized in transplantation are primarily collected in one of two ways. First, by directly accessing the bone marrow (bone marrow harvest), in which marrow is removed from the patient, usually by multiple aspirations of marrow from the posterior ileac crest, in a bone marrow harvest procedure performed in the operating room. A second collection method is performed by removal of mononuclear cells from the donor's peripheral blood (which contains a fraction of hematopoietic stem cells as well as other populations of cells including high numbers of T-cells. In this procedure peripheral blood stem cells are collected by apheresis following donor treatment with either chemotherapy (usually cyclophosphamide) or with the cytokine Granulocyte Colony Stimulating Factor (GCSF). Treatment with cyclophosphamide or GCSF functions to mobilize and increase the numbers of hematopoietic stern cells circulating in the blood.

Traditional bone marrow harvest procedures have several shortcomings:

To perform a harvest of 500-1000 milliliters of marrow, multiple separate entries into the marrow cavity are required to in order to remove a sufficient amount of bone marrow. A bone marrow aspiration needle (sharp metal trocar) is placed through the soft tissue, through the outer cortex of the ileac crest and into the marrow space. The aspiration needle enters less than 2 cm into the marrow cavity. Negative pressure is applied through the hollow harvest needle (usually by the operator pulling on an attached syringe into which 5-10 ml of marrow is aspirated). The needle and syringe are then removed and after removing the collected marrow, the aspiration needle accesses a separate location on the ileac bone for another aspiration. This is performed multiple times (on the order of 100-200 separate entries for an average patient) in order to remove a sufficient volume of bone marrow required for transplantation. Each puncture and entry into the marrow cavity accesses only a limited area of the marrow space, and the majority of practitioners only remove 5-10 milliliters of marrow with each marrow penetration. Pulling more marrow from a single marrow entry site otherwise results in a collected sample highly diluted by peripheral blood.

General anesthesia—The bone marrow harvest procedure requires general anesthesia. General anesthesia is required because the ileac crest is penetrated 100-300 times with a sharp bone marrow trocar. Local anesthesia is generally not possible given the large surface area and number of bone punctures required.

Recovery Time—The donor can take some time recovering from general anesthesia, and frequently suffers from days of sore throat, a result of the endotracheal intubation tube placed in the operating room.

Time consuming for patient—Pre-operative preparation, the harvest procedure, recovery from anesthesia, and an overnight observation stay in the hospital following the procedure is an imposition on the donor.

Time Consuming for the physician: In addition to general operating room staff, the traditional bone marrow harvest procedure requires two transplant physicians (each physician aspirating marrow from the left or right side of the ileac crest) and. Who spend approximately one hour each to perform the procedure.

Pain—Many donors experience significant pain at the site of the multiple aspirations (bone punctures) which persists for days to weeks.

Complications—Traditional bone marrow aspiration incurs a significant degree of contamination with peripheral blood. Peripheral blood contains high numbers of mature T-cells (unlike pure bone marrow). T-cells contribute to the clinical phenomenon termed Graft vs. Host Disease (GVHD), in both acute and chronic forms following transplant in which donor T-cells present in the transplant graft react against the recipient (host) tissues. GVHD incurs a high degree of morbidity and mortality in allogeneic transplants recipients.

Expensive—Cost of the procedure $10-15K, which includes costs for operating room time, anesthesia supplies and professional fees, and post-operative care and recovery.

Peripheral Blood Stem Cell Collection also has several shortcomings:

Slow and time consuming—Requires the donor to first undergo 7-10 or more days of daily subcutaneous injections with high doses of the cytokine GCSF prior to the harvest. These daily injections can be uncomfortable and painful. Peripheral blood stem cells can not be obtained without this 7+ day lead time.

Expense—Each day of apheresis costs approximately $3000 (including but not limited to the cost of the apheresis machine, nursing, disposable supplies and product processing) and the patient often has to come back on multiple days in order to obtain an adequate number of stem cells. Costs for the GCSF drug alone approximate $6,000-10,000 depending upon the weight of the patient (usually doses as 10 micrograms/kilogram/day).

Complications—Given the multiple days required to collect adequate numbers of hematopoietic stem cells, individual bags of peripheral blood product must processed and frozen separately. These bags are then thawed, and given back to the recipient patient at the time of transplant. The volume, and chemicals contained in the product freezing media can cause some mild side effects at the time of infusion.

Accordingly, there is a need for a minimally invasive, less expensive, time-efficient bone marrow harvest procedure with minimal complications which does not require general anesthesia, offers fast recovery time, and does not cause significant pain to the bone marrow donor.

SUMMARY

Device and method for rapid extraction of body tissue from an enclosed body cavity. Device comprises a hollow introduction cannula containing a trocar. Entry cannula and core element penetrate body tissue such as the marrow space contained within the ileac or other bone. Aspiration cannula is inserted through entry cannula into body tissue and advances through the body cavity. Within the aspiration cannula there may be a stylet (aspiration stylet), which can aid in the advance of the cannula through cavity and can be removed to facilitate extraction of body tissue through the aspiration cannula. Aspiration cannula has inlet openings near the distal tip through which tissue is aspirated. At the proximal end of aspiration cannula a negative pressure (suction) source provides controlled negative pressure enabling tissue to be aspirated through aspiration cannula into a collection reservoir. Aspiration cannula may be withdrawn and adjusted for multiple entries through the same tissue entry point, following different paths through tissue space for subsequent aspiration of more tissue.

DETAILED DESCRIPTION

Overview

Figure 1:
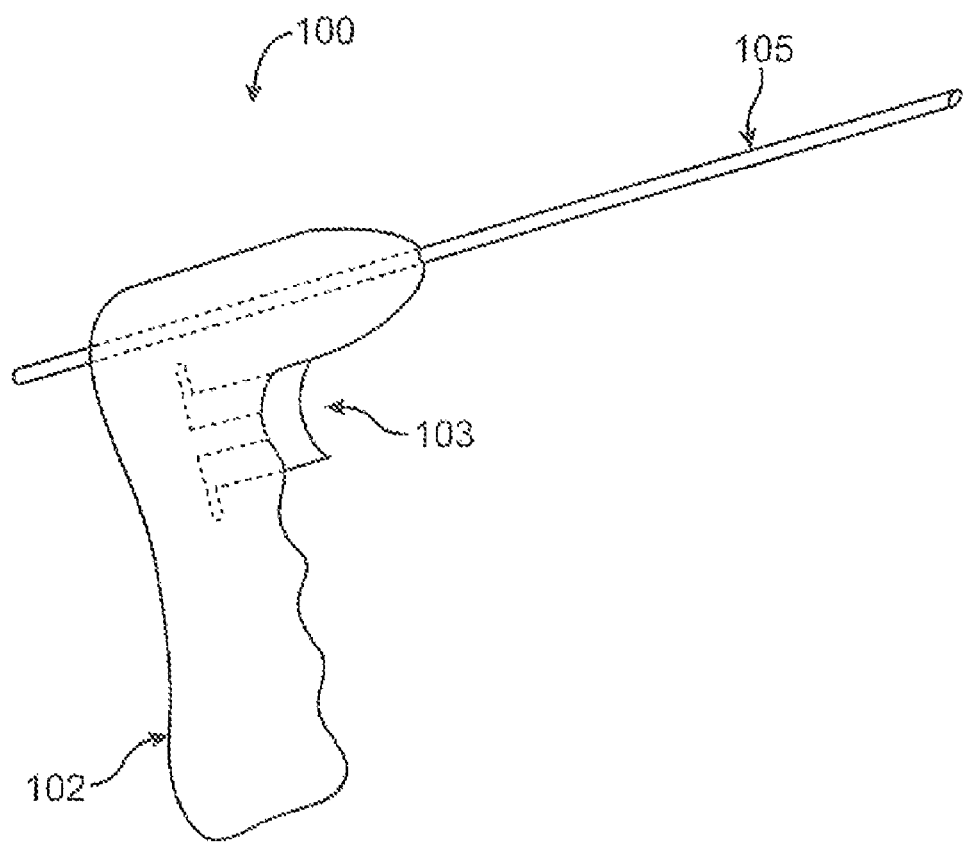
FIG. 1 is a diagram illustrating a device for rapid aspiration and collection of body tissue from within an enclosed body space, according to one embodiment of the present invention.

An apparatus is provided to aspirate bone marrow and/or tissue rapidly and for large volumes of bone marrow from the ileac, femur, or other marrow containing bone marrow cavities. The apparatus includes a lumen adapted to receive an elongated aspiration cannula. Following entry through the bone wall, the aspiration cannula may be controlled to move in a non-linear fashion within the marrow cavity so that it can access a majority of bone marrow space through a single point of entry. Suction may be applied to the aspiration cannula to harvest the bone marrow or other aspiratable substances. If it is determined that a threshold amount of aspiratable substance has not been obtained, the aspiration cannula may be adjusted to enable further harvesting from the same bone wall entry or from an alternative bone wall entry.

Device and method for rapid, minimally invasive, aspiration and collection of body tissue from within an enclosed body space, as described herein, provide following advantages over the existing harvest systems:

Efficacy—traditional extraction accesses only a small volume of marrow with each needle insertion and negative pressure draws blood from surrounding capillaries and dilutes the extract. Invention described herein moves to directly contact more of the marrow space and aspirates a more concentrated, less diluted extract. The extracted bone marrow is more concentrated in stem cells because the device penetrates the pelvic cavity more broadly and thus the extracted material is less diluted with blood drawn into the void created by the extraction. The decreased numbers of contaminating T-cells will likely lead to less Graft vs. Host Disease (GVHD) in allogeneic bone marrow recipients. Less total volume of bone marrow will need to be removed (as it is more concentrated).

Efficiency—the harvest performed with the invention described herein proceeds faster than conventional trocar harvest because only one access point into the marrow cavity is needed on each side of the body and less total volume of material is extracted (as it is more concentrated). One possible marrow access point is the easily accessible anterior ileac crest access site, which is easier to find and access on a broad array of patients (from thin to obese) and utilizing this entry site will also reduce harvest time.

Cost—the procedure described herein will be considerably less expensive than the conventional procedure because described invention requires no operating room time, reduced support personnel, and no anesthesiologist. In terms of peripheral blood hematopoietic stem cell aspiration via apheresis—the $6,000-$10,000 cost for GCSF cytokine treatments and several lengthy (4-20+ hours each) apheresis procedures will be negated.

Convenience: There is no significant lead or preparative time required to perform a bone marrow harvest, as the procedure can be performed without an operating room, or general anesthesia by a single operator. Critically ill, or bone marrow donors who could not readily tolerate traditional harvest methods would benefit. Marrow and or stem cells derived from marrow could be obtained rapidly for use in follow-on therapeutic interventions.

Qualities & Benefits

This device and method could be applied to a range of soft tissue extractions. Specific uses include, but are not limited to, the aspiration of bone marrow, removal of fat, aspiration of blood and muscle. We consider the bone marrow harvest application further for the sake of illustration.

To provide a bone marrow aspiration device for the rapid extraction of small or large volumes of bone marrow from the ileac, femur or other marrow containing bone marrow cavities or spaces.

To aspirate tissue such as marrow through a single skin and bone puncture site into the marrow cavity.

The ability to control directionality of described invention within the marrow cavity such that it can access majority of bone marrow space through a single point of entry.

To provide controlled aspiration suction through described invention of bone marrow or other aspiratable substance such as fat.

Described invention will significantly shorten bone marrow harvest time, not require general anesthesia, and result in cost reductions compared to traditional bone marrow harvest of peripheral blood stem cell collection.

To enable access to multiple diagnostic samples of bone marrow from disparate sites within the marrow cavity FIG. 1 is a diagram illustrating a device 100 for rapid aspiration and collection of body tissue from within an enclosed body space (hereinafter referred to as "aspiration device"), according to one embodiment of the present invention. Aspiration cannula 105 couples to optional handle 102 for ease of holding and operation.

Figure 2:
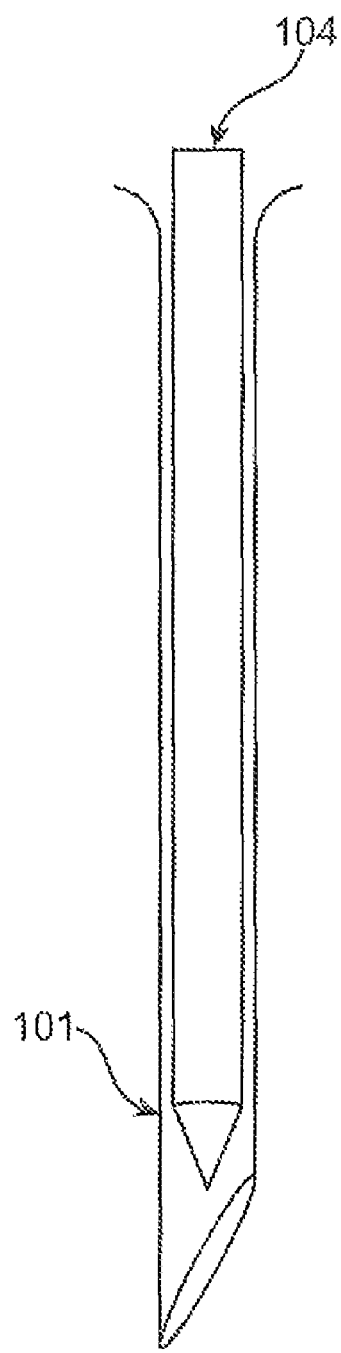
FIG. 2 illustrates entry cannula 101 with core element 104, according to one embodiment of the present invention.

FIG. 2 illustrates entry cannula 101 with core element 104, according to one embodiment of the present invention. Entry cannula 101 comprises a needle with hollow central lumen accommodating a core element 104 for initial insertion into a bone marrow cavity or body tissue, for example through the anterior ileac crest, posterior ileac crest, lateral trocanter of the femur, or other location for aspiration bone marrow or other body tissue. Aspiration cannula 105 enters the body tissue through the entry provided by entry cannula 101.

Core element 104 comprises a trocar or other element for breaking or piercing through the bone wall (or other tissue boundary) and creating an entry for subsequent aspiration. Optionally, entry cannula 101 is strong enough, to break or pierce through the bone wall without the help of core element 104.

In an alternative embodiment, an entry in the bone wall is created using a tool other than entry cannula 101 and/or core element 104, such as a separate trocar or other sharp tool for breaking or piercing the bone wall, preparing the bone (or other tissue area) for the entry of aspiration cannula 105.

Once an entry is created into the bone marrow and entry cannula 101 enters the bone marrow (or other body tissue intended for aspiration), core element 104 is removed, leaving a hollow entry lumen with access to the medullary cavity.

Figure 3:
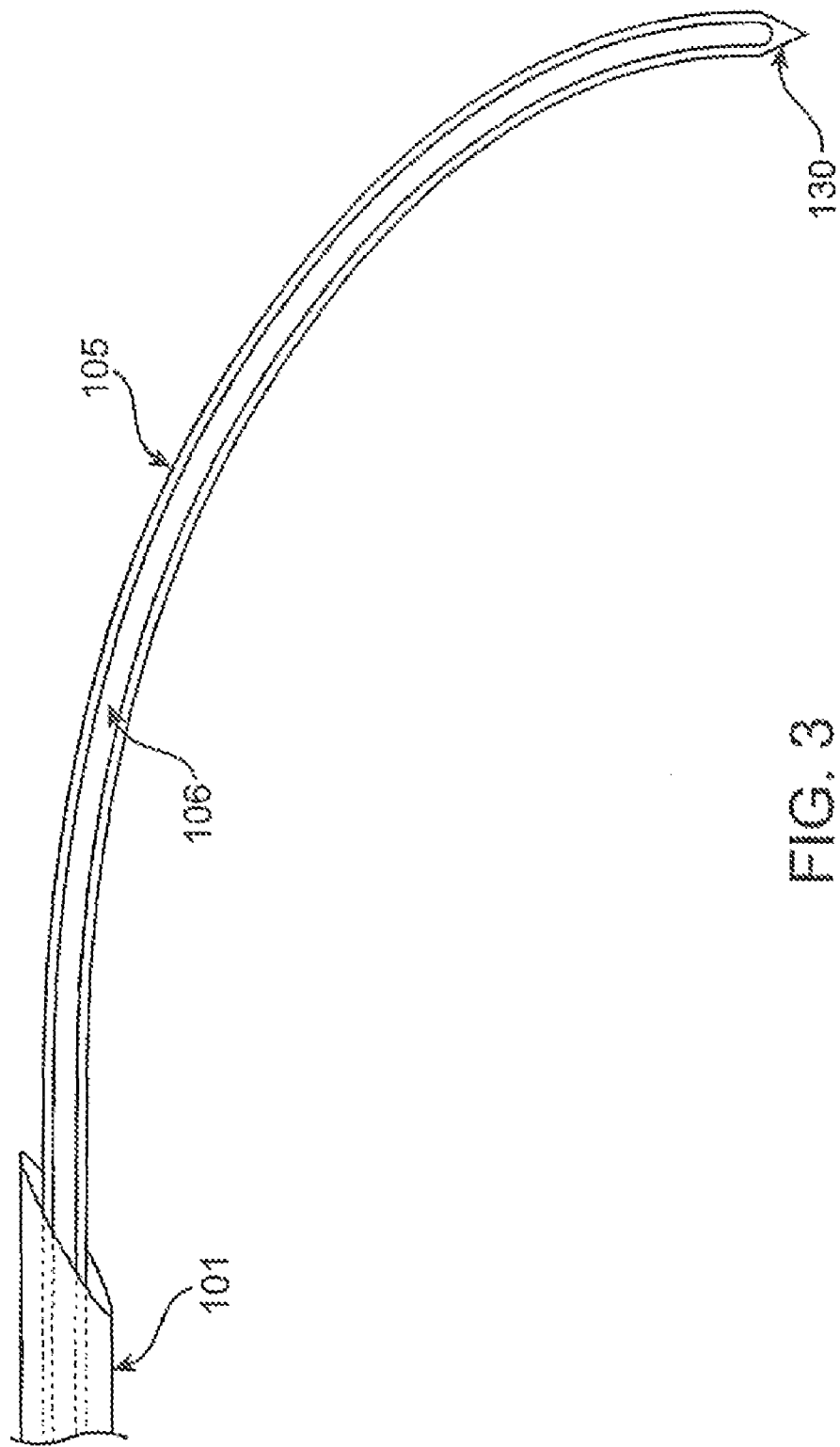
FIG. 3 illustrates aspiration cannula, according to an embodiment of the present invention.

FIG. 3 illustrates aspiration cannula 105, according to an embodiment of the present invention. Aspiration device 100 comprises aspiration cannula 105, for entering through the hollow entry cannula 101 and through the bone wall (or other tissue area) entry into the marrow space. Aspiration cannula 105 comprises flexible material allowing for curvature for following bone marrow cavity (or other tissue area). In one embodiment, aspiration cannula 105 has a length of 6-16 inches. The size of the aspiration cannula 105 may vary based on the size and anatomy of the patient and/or the bone marrow cavity (or other body tissue area) intended for harvest.

Aspiration cannula 105 optionally comprises a stylet 106 ("aspiration stylet"). When inserted into aspiration cannula 105, optional aspiration stylet 106 provides structural strength and aids in (for example the intramedullary bone marrow space of the ileac or femur bone) advance of aspiration cannula 105 through the marrow space (or other tissue area). Optionally, aspiration stylet 106 comprises a preset degree of curvature prior to and following entry into body cavity through entry cannula 101. Aspiration stylet 106 can be removed from aspiration cannula 105 to allow aspiration of marrow (or other body tissue) through aspiration cannula 105. Optionally, aspiration stylet 106 is used to remove and/or disrupt blockages within aspiration cannula 105, such as bone fragments, fat, coagulation, blood clots or other substance which may be blocking aspiration.

Figure 4A:
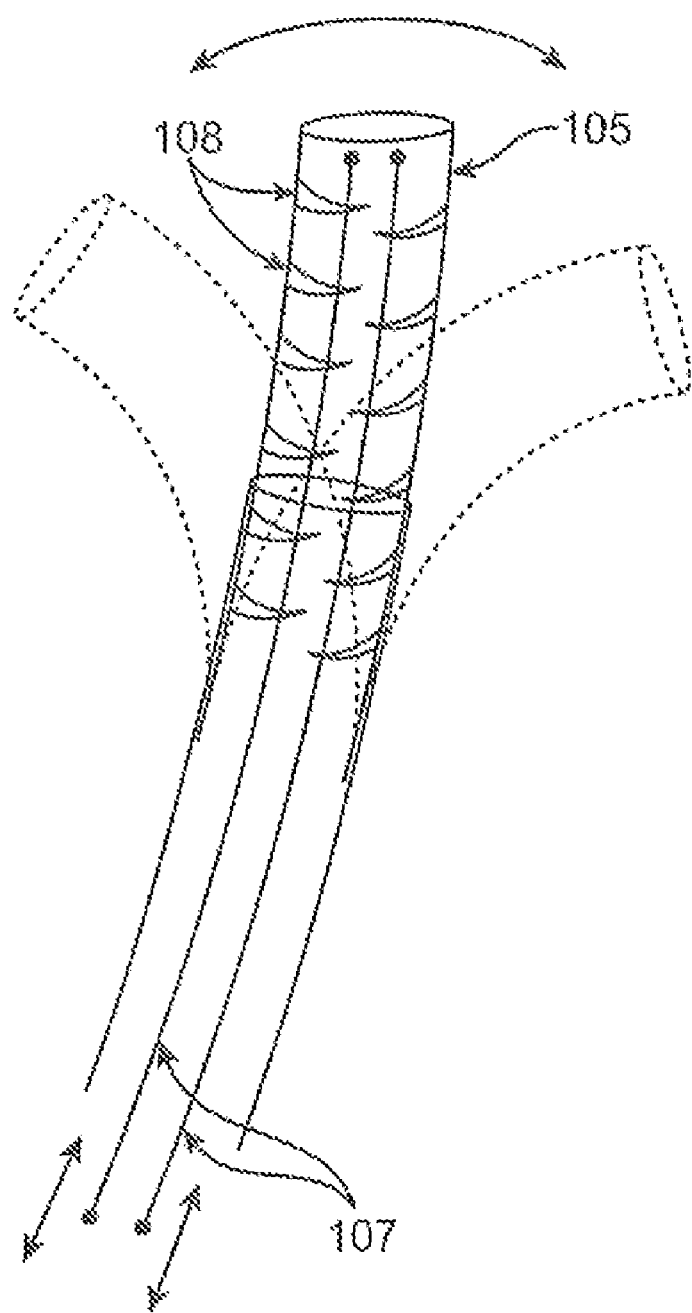
FIG. 4a shows aspiration cannula with one or more steering wires, according to an embodiment of the present invention.
Figure 4B:
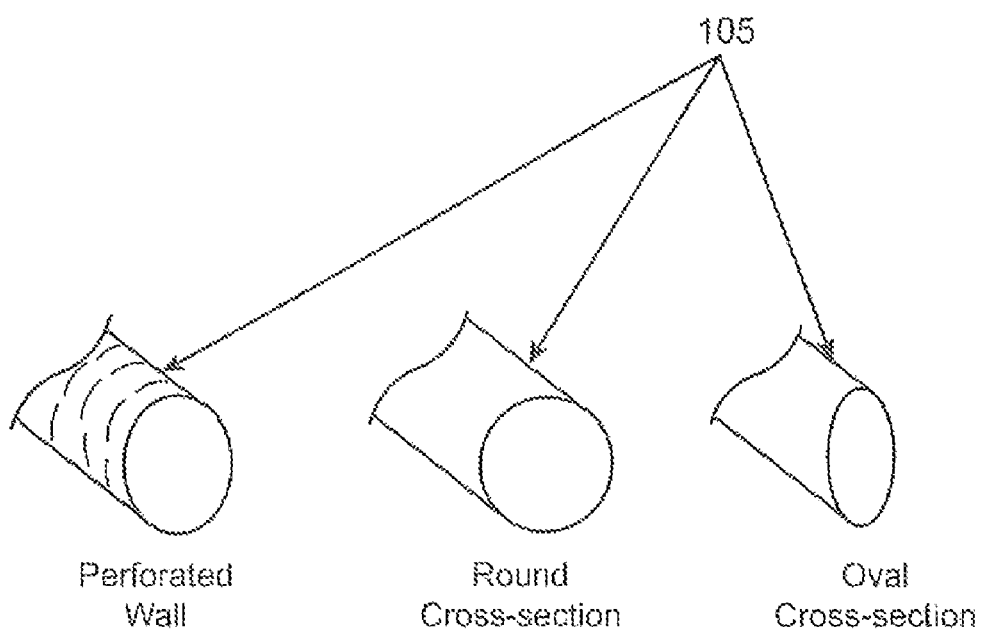
FIG. 4b shows perforated wall and cross-section of aspiration cannula, according to an embodiment of the present invention.

Optionally, aspiration cannula 105 is steerable and directable. FIG. 4a shows aspiration cannula 105 equipped with one or more steering wires 107, according to an embodiment of the present invention. Contraction or pulling of a steering wire 107 by operator results in curvature of aspiration cannula 105 according to the direction and/or location of contracted or pulled steering wire 107. Optionally, and as shown in FIG. 4b, aspiration cannula 105 comprises flexible material and/or perforations 108 on the wall of aspiration cannula 105 allowing for curvature and increased lateral flexibility, and/or oval cross-section for limiting axes of curvature. Optionally, aspiration cannula 105 comprises material with shape-memory, for example a shape memory alloy (such as Nitinol), a shape memory plastic, or other metallic or non-metallic material with shape-memory, for example resulting in a curved profile of aspiration cannula 105, for providing directionality to aspiration cannula 105 upon aspiration cannula's 105 entry into the body tissue or body cavity.

Figure 4C:
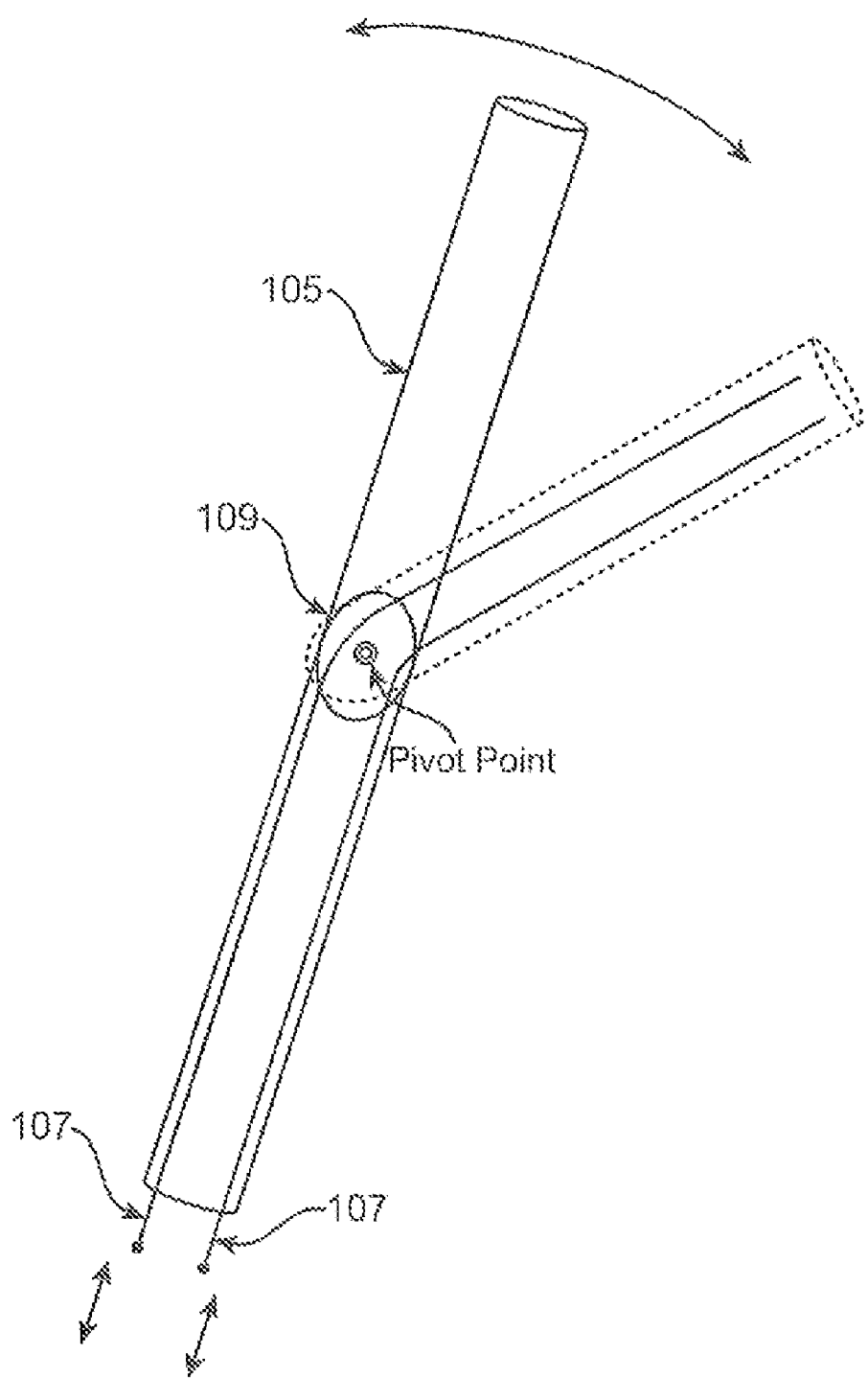
FIG. 4c shows universal joint of aspiration cannula, according to an embodiment of the present invention.

Optionally, as shown in FIG. 4c, aspiration cannula 105 comprises a universal joint 109 for providing a pivot point, allowing the contraction or pulling of steering wires 107 to result in steering and/or change of direction of aspiration cannula 105.

Figure 4D:
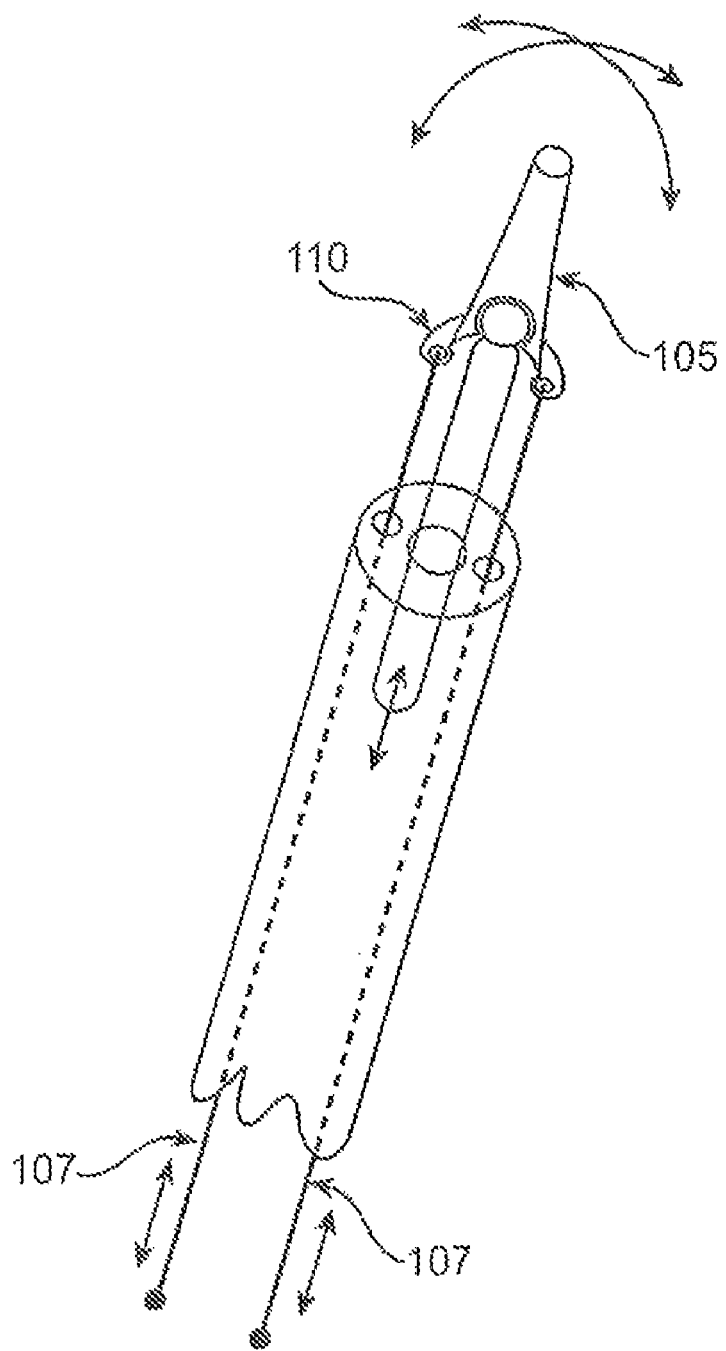
FIG. 4d shows squash plate of aspiration cannula, according to an embodiment of the present invention.

Optionally, as shown in FIG. 4d, aspiration cannula 105 comprises a squash plate 110, allowing the contraction or pulling of steering wires 107 to result in steering and/or change of direction of aspiration cannula 105.

Figure 4E:
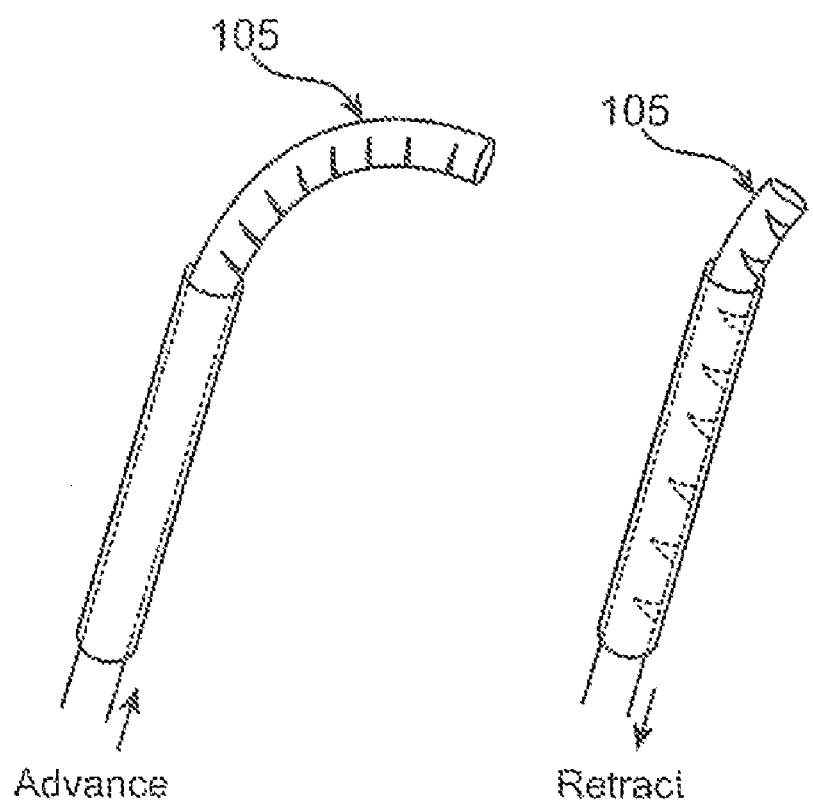
FIG. 4e shows preset degree of curvature of aspiration cannula, according to an embodiment of the present invention.

Optionally, as shown in FIG. 4e, aspiration cannula 105 a preset degree of curvature such that after passing through entry cannula 101 and into the bone cavity, aspiration cannula 105 assumes a curvature according to the preset curvature, thereby assisting its direction when advancing within the cavity.

Figure 5:
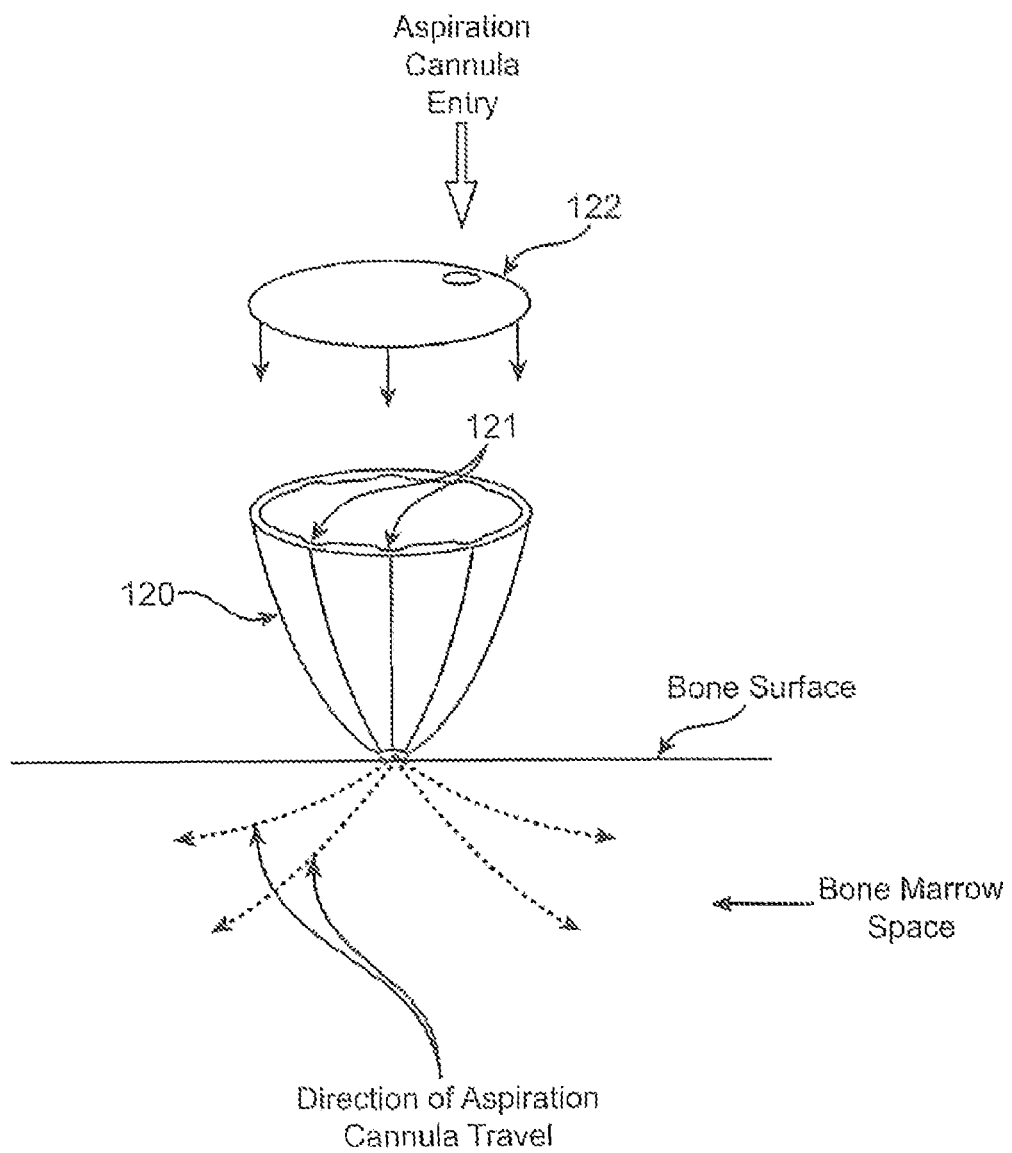
FIG. 5 illustrates a groove cup, according to an embodiment of the present invention.

Optionally and as illustrated in FIG. 5, a groove cup 120 is used for guiding aspiration cannula 105 into bone marrow (or other body tissue). Groove cup 120 comprises one or more grooves 121, a groove 121 providing directional entry of aspiration cannula 105 into bone marrow. Placement of aspiration cannula 105 into an appropriate groove 121 allows entry of aspiration cannula 105 into bone marrow with directionality according to selected groove 121. Optionally, groove cup 120 has groove dial 122 for convenient selection of groove 121 and guiding of aspiration cannula 105 through selected groove 121 and into the bone marrow space.

Figure 6A:
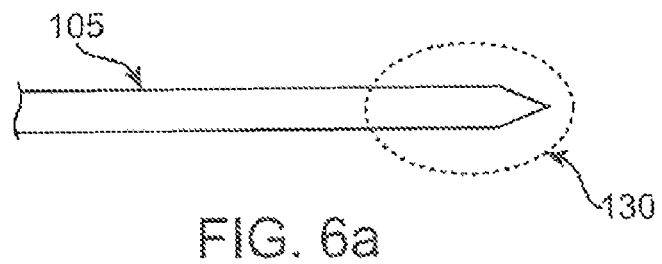
FIG. 6a illustrates a distal tip, according to an embodiment of the present invention.

According to one embodiment of the present invention and as shown in FIG. 6a, aspiration device 100 comprises a distal tip 130 at the distal end of aspiration cannula 105 or at the distal end of optional aspiration stylet 106, for advancing through the bone marrow cavity (or other body tissue).

Figure 6B:
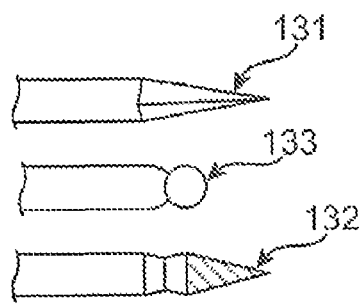
FIG. 6b illustrates a sharp tip, a rotating drill tip and a sonication device, according to an embodiment of the present invention.
Figure 9:
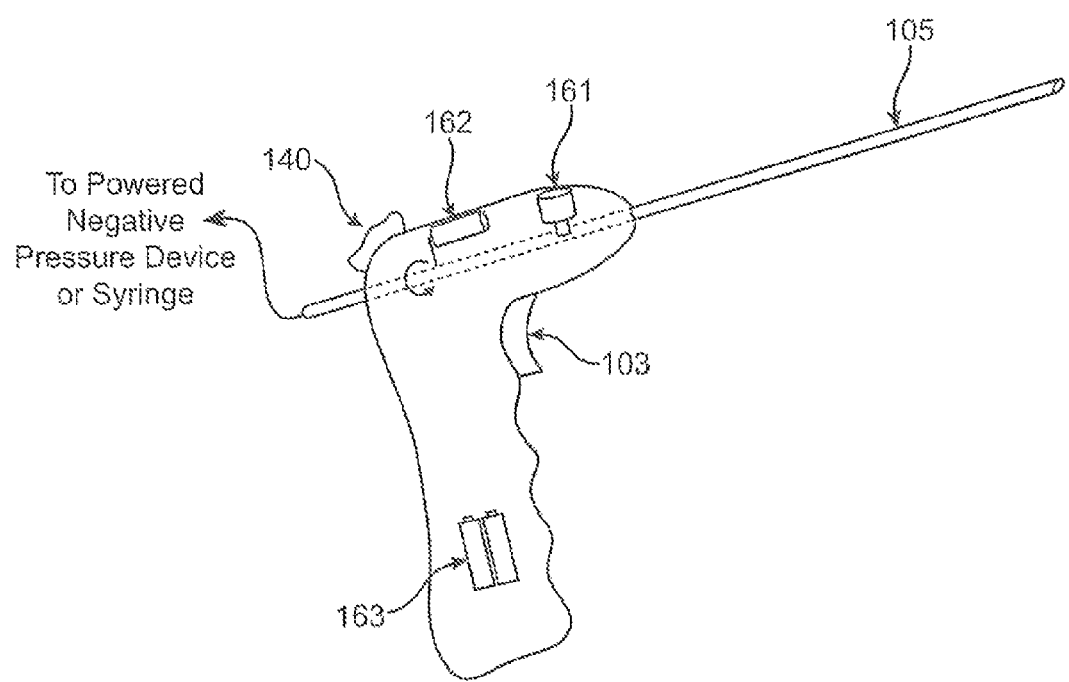
FIG. 9 illustrates optional reservoir for materials or liquids for administration, and optional electric motor, according to an embodiment of the present invention.

As shown in FIG. 6b, Distal tip 130 comprises a sharp tip 131, a rotating drill tip 132 (manual or powered, for example powered by an electric motor 162 as shown in FIG. 9, with motor 106 using power from batteries 163 or from an outside electrical source), optionally comprising a variable speed controllable and/or reversible drill tip), a sonication device 133 (for tissue disruption) or other tissue disruptor for penetrating and/or advancing through the bone marrow (or other body tissue).

Figure 6C:
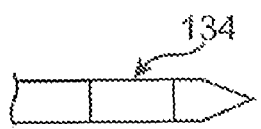
FIG. 6c illustrates a sonication device and an ultrasound transducer, according to an embodiment of the present invention.

Optionally and as shown in FIG. 6c, distal tip 130 comprises an ultrasound transducer or other navigation element 134 for providing navigation and/or visual guidance within bone marrow space (or other body tissue) to assist steering of aspiration cannula 105, such as providing feedback indicating proximity of distal tip 130 or aspiration cannula 105 to bone wall (or to other tissue boundary).

Figure 6D:
FIG. 6d illustrates an example of a distal tip modified to have a rounded blunt tip, according to an embodiment of the present invention.

Optionally, distal tip 130 is modified such that it cannot puncture out of the body space or cavity (such as bone marrow space or other body tissue area) but instead moves sideways along a wall or boundary upon encountering such wall or boundary. FIG. 6d shows an example of a distal tip 130 modified to have a rounded blunt tip 135 to behave in this way.

Optionally, aspiration device 100 comprises a combination of radio-opaque and/or radio-transparent material for use in conjunction with an imaging device, such as an X-ray or ultrasound device, for visual location of the aspiration cannula 105. For example, aspiration cannula 105 and/or other parts may be radio-transparent, with aspiration cannula 105 comprising a radio-opaque visual guide (for example using X-Rays or other radiographic methods) along the length of aspiration cannula 105 (such as a strip with visual distance markings showing how far aspiration cannula 105 has advanced into bone marrow space or other body tissue area).

Figure 7:
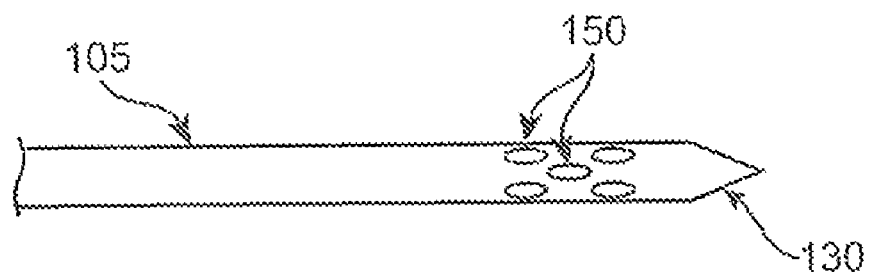
FIG. 7 illustrates inlet openings near the distal tip of aspiration cannula, according to an embodiment of the present invention.

As shown in FIG. 7 according to one embodiment of the present invention, aspiration cannula 105 comprises one or more inlet openings 150 near the distal tip 130 through which marrow or other tissues can be aspirated by the application of negative pressure. A negative pressure element couples to the proximal end of aspiration cannula 105 for application of negative pressure resulting in aspiration (suction) of bone marrow (or other body tissue) into a reservoir for bone marrow (or for other body tissue). In one embodiment, the negative pressure element comprises a syringe. In another embodiment, the negative pressure element comprises a powered device (such as a wall mounted continuous negative pressure device or other powered device for providing controlled negative pressure). Handle 102 has optional trigger element 103 (as shown in FIG. 9) for controlling aspiration negative pressure or degree of suction, for example by controlling a pressure gate for allowing proper degree of negative pressure.

Optionally, aspiration device 100 comprises a pain attenuating device for dampening pain and/or sensation during the aspiration procedure. For example, aspiration cannula 105 may comprise one or more sites for providing electrical nerve stimulation to the harvest area resulting in pain attenuation (see U.S. Pat. No. 6,159,163, Strauss et al., May 1998).

Optionally, a lining of anticoagulant material (such as heparin) on the inside wall of entry cannula 101 and/or aspiration cannula 105 prevents blood and/or marrow from coagulating and hindering aspiration of marrow or body tissue. Optionally, entry cannula 101 and/or aspiration cannula 105 are flushed with anticoagulant solution to prevent and/or dissolve clots.

Figure 8:
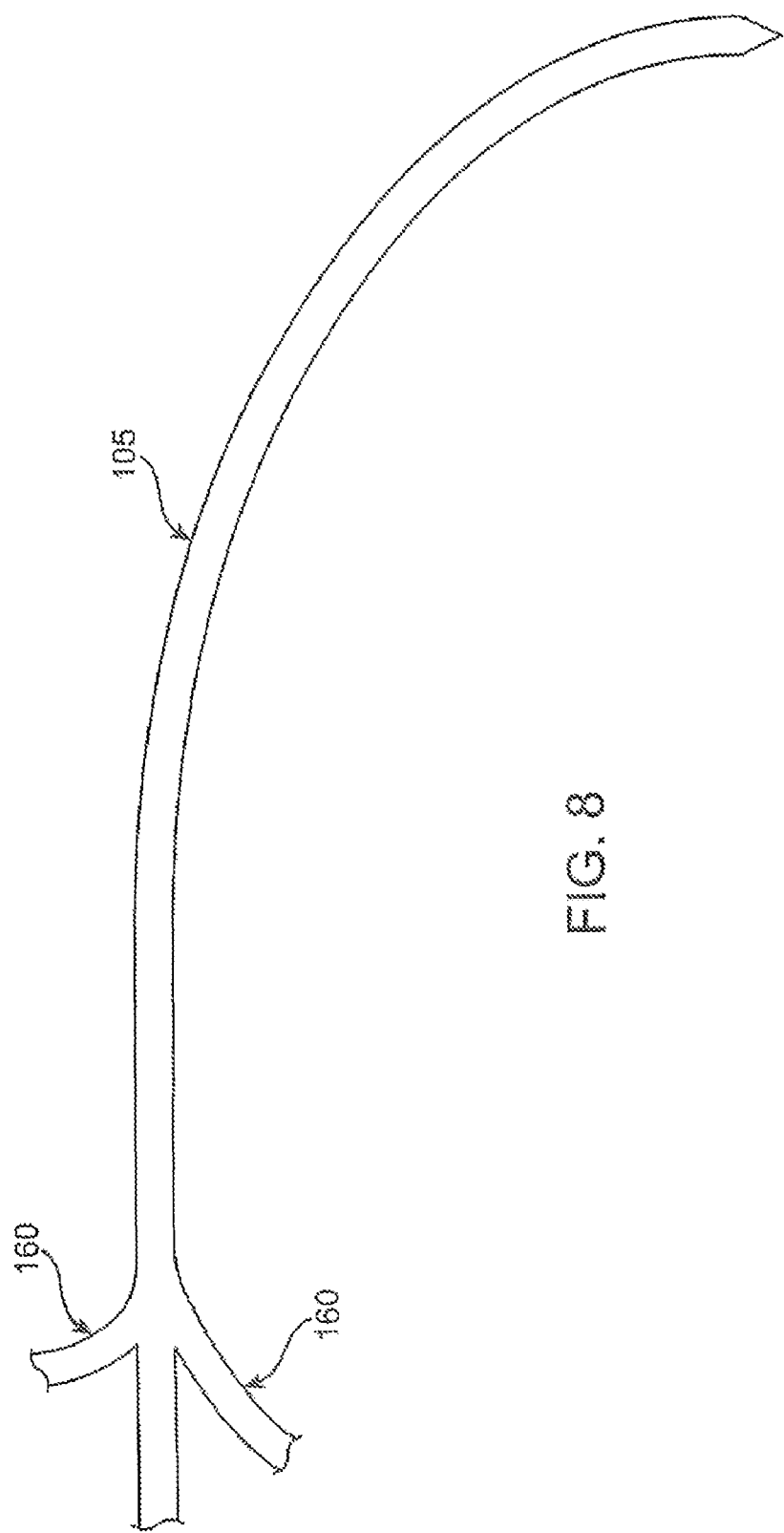
FIG. 8 illustrates additional ports of aspiration cannula, according to an embodiment of the present invent ion.

Optionally and as shown in FIG. 8, aspiration cannula 105 has one or more additional ports 160 through which material or liquid (such as anticoagulant described above) can be administered. An optional port in the aspiration cannula 105 allows administration of a stylet into the aspiration cannula for unblocking or removing any blood or tissue clots which may occur. Aspiration device 100 comprises optional reservoir 161 for materials or liquids (such as anticoagulant described above) for administration, as shown in FIG. 9.

FIG. 9 also shows an example of a steering control 140 for steering, guiding, advancing, and/or retracting aspiration cannula 105 while aspiration cannula 105 in outside and/or inside bone marrow space (or other body tissue area). In the embodiment described above, wherein aspiration cannula 105 comprises one or more steering wires 107, activation of steering control 140 causes contraction or pulling of one or more steering wires 107 resulting in curvature and/or change of direction of aspiration cannula 105. In one embodiment, steering control 140 comprises a manual control, such as a handle, which can be moved to steer or manipulate aspiration cannula 104. For example, forward movement of apparatus 100 causes advancement of aspiration cannula 105 and backward movement of apparatus 100 results in withdrawal of aspiration cannula 105, whereas movement of steering control 140 handle to different-sides (for example to the left, right, up or down) causes aspiration cannula 105 to curve to the corresponding side (for example to the left, right, up or down). In another embodiment, steering control 140 comprises a powered control, such as a multi-way thumb-stick or one or more buttons for steering and/or advancing and retracting aspiration cannula 105 (shown in FIG. 9).

The length and/or diameter and/or flexibility and/or curvature of entry cannula 101 and/or aspiration cannula 105 can be chosen to accommodate different anatomies (such as corresponding to different ages, bone sizes, amount of body fat, and other factors distinguishing patients) and for the harvest of a range of body tissues, such as bone marrow, fat (liposuction), fluid in the abdomen of a patient (with liver disease for example), or possibly for minimally invasive removal of a soft tissue mass such as a tumor. For example, a child may require a shorter, more flexible aspiration cannula 105. As another example, aspiration of bone through the lateral trocanter of the femur, or via the anterior ileac crest may require a shorter entry cannula 10I and/or aspiration cannula 105 than aspiration of bone marrow through the posterior ileac crest which may have more soft tissue above the bone.

There is growing body of scientific evidence that bone marrow derived stem cells can be utilized to regenerate or improve function of damaged myocardium following a myocardial infarction (MI), and may be useful in treating and preventing congestive heart failure. The ability to rapidly and easily obtain bone marrow derived stem cells for use in cardiac regeneration and other regenerative stem cell based therapies may be crucial. For example; a patient who has recently been diagnosed with a significant myocardial infarction is brought to the catheterization suite, where interventional cardiologists perform angioplasty to open up a blocked coronary artery. Before, during or after the angioplasty procedure, a significant volume of bone marrow would be harvested using aspiration device 100. The bone marrow could be rapidly processed to enrich for hematopoietic stem cells or other populations or fraction of cells contained within bone marrow. These cells would then be delivered via catheter of other delivery device to the region of the heart which has undergone infarction and injury or death secondary to acute cardiac ischemia or other acute or chronic insults to the myocardial tissue. The delivered bone marrow or stem cell component contributes to regeneration of the myocardium or otherwise acts to improve cardiac function in the area of the infarct and leads to improved cardiac function and patient functional status and mortality. Optionally, marrow could be harvested separately from the initial cardiac catheterization procedure (for example 7 days after the MI, and in a separate procedure, stem cells or marrow enriched for stem cells could he delivered by any number of delivery mechanisms, for example by intracoronary or intramuscular injection. Use of a minimally invasive harvest device 100 would facilitate ease of harvest in patients who may be critically ill and not able to easily tolerate traditional marrow harvest procedures.

Figure 10A:
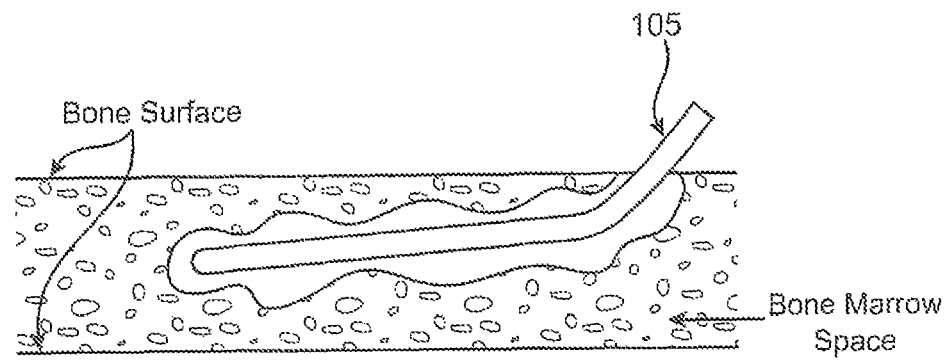
FIG. 10a illustrates how the device for rapid aspiration and collection of body tissue from within an enclosed body space enables a single operator to harvest marrow through one bone entry point, in accordance with an embodiment of the present invention.
Figure 10B:
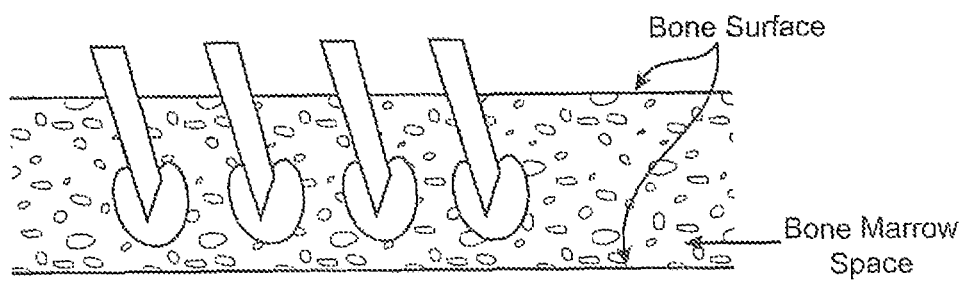
FIG. 10b illustrates how a conventional bone marrow harvest procedure uses several bone punctures and separate small volume aspirations.

Advantageously, aspiration device 100 considerably improves on existing bone marrow harvest procedures by enabling a single operator to harvest marrow through one bone entry point, as illustrated in FIG. 10a, instead of several dozen to hundreds of bone punctures and separate small volume aspirations, as shown in FIG. 10b.

Figure 11:
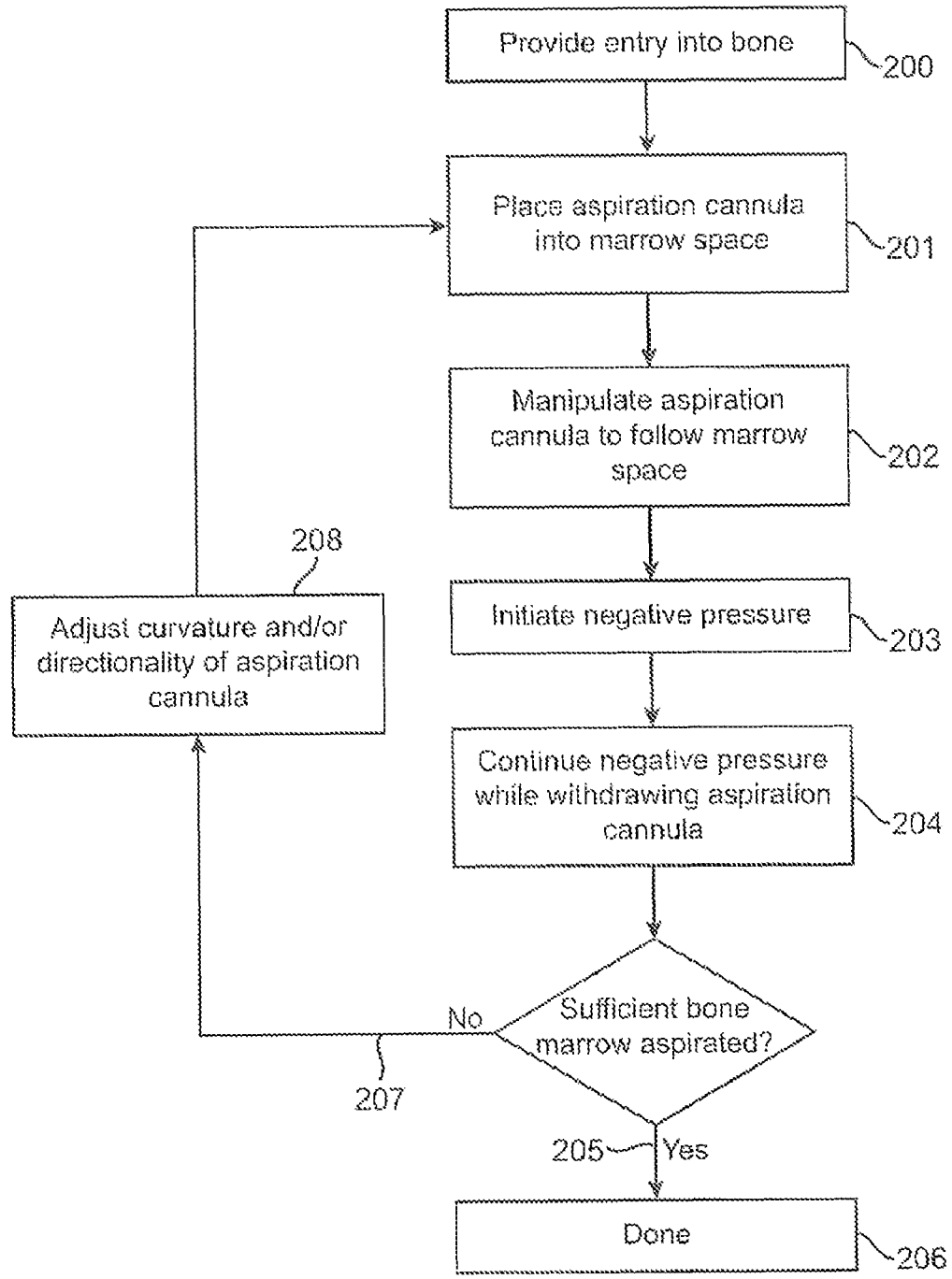
FIG. 11 illustrates a method for rapid aspiration and collection of body tissue from within an enclosed body space, according to an embodiment of the present invention.

FIG. 11 illustrates a method for rapid aspiration and collection of body tissue from within an enclosed body space, according to an embodiment of the present invention. After providing 200 an entry into the marrow using entry cannula 101 (and/or using core element 104, in which case the core element 104 of the entry cannula 101 is removed after providing the entry), a hollow entry lumen is left with access to the medullary cavity. Next, aspiration cannula 105 is placed 201 through the hollow entry cannula 101 and introduced into the marrow space. The aspiration cannula 105 is then manipulated 202 (using steering control 140) to move and follow the bone marrow cavity, assisted by the distal tip 130 the aspiration cannula.

As described above, aspiration cannula 105 will have a degree of flexibility and/or curvature allowing it to follow the cavity (for example the intramedullary bone marrow space of the ileac or femur bone), and an optional ultrasound transducer device at the distal tip 130 of the aspiration cannula 105 can aid movement and define width of the cavity.

Figure 12:
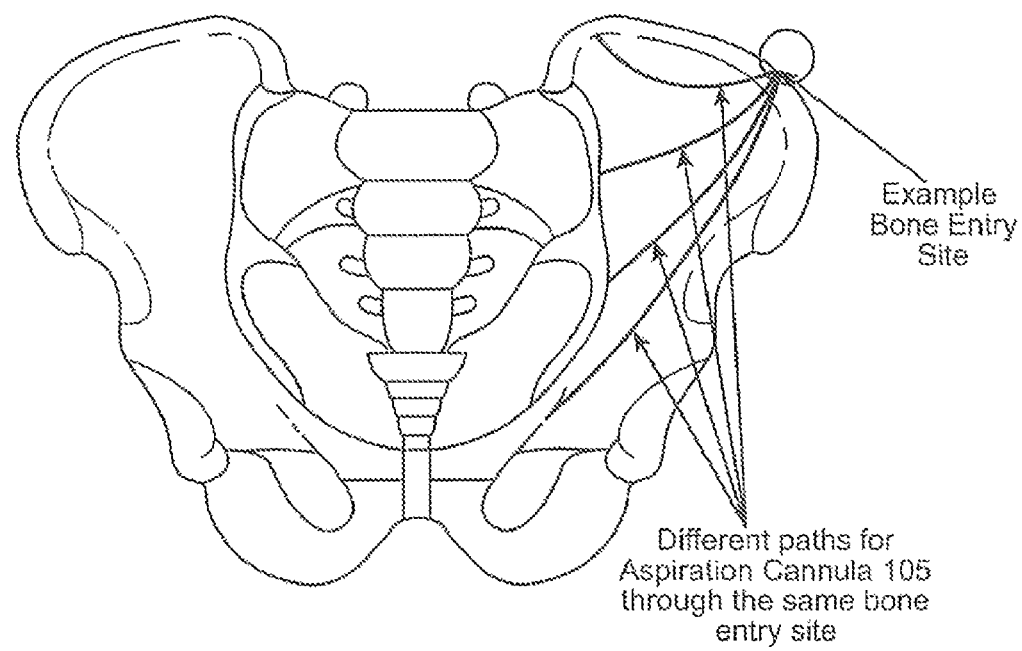
FIG. 12 shows entry site on one side of the body with multiple aspiration paths, according to an embodiment of the present invention.
Figure 12:
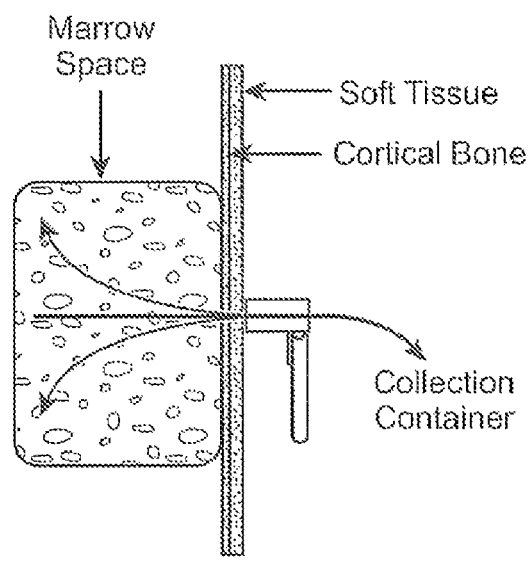

Once the aspiration catheter is fully introduced into the body cavity, negative pressure is initiated 203, using for example a syringe or a powered negative pressure device as described above. As bone marrow is aspirated the aspiration cannula 105 is slowly withdrawn 204, with aspiration continuing as the aspiration cannula 105 is withdrawn. If 205 sufficient amount of bone marrow is aspirated 205, the aspiration process is complete 206. Otherwise 207, after withdrawal of aspiration cannula 105, the curvature and/or directionality of the aspiration cannula 105 is adjusted 208, and aspiration cannula 105 is redirected through the entry into the bone marrow space and manipulated to follow a different path through the space and aspirating more bone marrow. This process can be repeated for example 3-4 times, resulting in its aspiration of bone marrow from the majority of the bore marrow space (for example the ileac crest). This process can be repeated 011 both sides of the body as needed (FIG. 12 shows an entry site on one side of the body with multiple aspiration paths).

As described above, there is the option of utilizing one or more aspiration cannulae 105 with preset or modifiable degrees of curvature and/or length and/or diameter and/or flexibility to adapt to different individual patients' anatomy and degree of ileac or other bone anatomy. As described above, aspirated bone marrow will go directly into bone marrow reservoir or container through a closed system for initial storage and/or follow-on manipulation (such as filtering, stem cell enrichment, or other follow-on manipulation or treatment of bone marrow).

The apparatus and method shown herein provide many advantages for rapid aspiration and collection of body tissue from within an enclosed space. The directional control of the aspiration cannula by the operator enables the cannula to directly contact more of the marrow space and thereby aspirate a bone marrow that is more concentrated with stem cells than that available in the prior art. In addition, the harvest performed with the apparatus shown herein proceeds faster than prior art harvesting with a trocar since only one access point is required on each side of the body and less total volume of material is extracted. Finally, the procedure outlined above requires less time and reduced support personnel, thereby reducing costs for a procedure for harvesting bone marrow and/or tissue.

Foregoing described embodiments of the invention are provided as illustrations and descriptions. They are not intended to limit the invention to precise form described. Other variations and embodiments are possible in light of above teachings, and it is thus intended that the scope of invention not be limited by this Detailed Description, but rather by Claims following.

We claim:

1. A method for aspirating bone marrow and introducing at least one enriched population of cells into a body, comprising:
   introducing a drill tip attached at a distal end of an aspiration cannula into a bone marrow cavity through an entry port defined along the cavity, wherein the cannula has a flexible length which is deflectable in all directions relative to a proximal end of the length which is coupled to a handle;
   advancing the aspiration cannula along a first path within the cavity while rotating the drill tip, wherein the drill tip comprises a proximal fluted portion that is tapered in a distal direction from a proximal end of the drill tip and a distal portion having a rounded blunt tip, where the drill tip terminates at the rounded blunt tip such that the drill tip moves sideways upon encountering a surface of cortical bone within the cavity without causing trauma to the surface;
   aspirating a first portion of bone marrow from the cavity into one or more openings defined near the drill tip while rotating the drill tip;
   processing the aspirated bone marrow to enrich at least one population of cells contained therewithin; and,
   introducing the enriched at least one population of cells into a tissue region of interest.

2. The method of claim 1 wherein aspirating further comprises withdrawing the aspiration cannula proximally along the first path while further aspirating the bone marrow into the aspiration cannula via the one or more openings.

3. The method of claim 1 wherein the entry port is along an ileac crest.

4. The method of claim 1 wherein advancing the aspiration cannula comprises inhibiting the drill tip from puncturing through the surface of cortical bone such that the aspiration cannula is retained within a medullary cavity.

5. The method of claim 1 further comprising piercing through a wall of the cortical bone to create the entry port prior to the step of introducing.

6. The method of claim 5 wherein piercing through the wall of the cortical bone comprises piercing via an entry cannula through which the aspiration cannula is introduced.

7. The method of claim 1 wherein advancing the aspiration cannula comprises directing the drill tip to follow the first path.

8. The method of claim 1 further comprising, after aspirating a first portion, redirecting the aspiration cannula such that the cannula advances into the marrow cavity along a second path within the marrow cavity, where the second path is different from the first path.

9. The method of claim 1 wherein processing comprises intra-operatively enriching the at least one population of cells.

10. The method of claim 1 wherein processing comprises post-operatively enriching the at least one population of cells.

11. The method of claim 1 wherein processing comprises enriching hematopoietic or mesenchymal stem cells contained within the aspirated bone marrow.

12. The method of claim 1 wherein introducing comprises delivering the enriched at least one population of cells via catheter directly into the tissue region of interest.

13. The method of claim 1 wherein introducing comprises delivering the enriched at least one population of cells to the tissue region of interest via intramuscular injection into a patient body.

14. The method of claim 1 wherein introducing comprises delivering enriched hematopoietic or mesenchymal stem cells into an infarcted or injured coronary tissue region.

15. A method for aspirating bone marrow and introducing at least one enriched population of cells into a body, comprising:
   introducing a drill tip attached at a distal end of an aspiration cannula into a bone marrow cavity through an entry port defined along the cavity, wherein the cannula has a flexible length which is deflectable in all directions relative to a proximal end of the length which is coupled to a handle;
   advancing the aspiration cannula along a first path within the cavity while rotating the drill tip, wherein the drill tip comprises a proximal fluted portion that is tapered in a distal direction from a proximal end of the drill tip and a distal portion having a rounded blunt tip, where the drill tip terminates at the rounded blunt tip such that the drill tip moves sideways upon encountering a surface of cortical bone within the cavity without causing trauma to the surface;
   inhibiting damage to stem cells from the bone marrow while rotating the drill tip;
   aspirating a first portion of bone marrow from the cavity into one or more openings defined near the drill tip while rotating the drill tip;
   processing the aspirated bone marrow to enrich stem cells contained therewithin; and,
   introducing the enriched stem cells into an injured tissue region of interest.

16. The method of claim 15 wherein the entry port is along an ileac crest.

17. The method of claim 15 wherein advancing the aspiration cannula comprises inhibiting the drill tip from puncturing through the surface of cortical bone such that the aspiration cannula is retained within a medullary cavity.

18. The method of claim 15 further comprising piercing through a wall of the cortical bone to create the entry port prior to the step of introducing.

19. The method of claim 18 wherein piercing through the wall of the cortical bone comprises piercing via an entry cannula through which the aspiration cannula is introduced.

20. The method of claim 15 wherein advancing the aspiration cannula comprises directing the drill tip to follow the first path.

21. The method of claim 15 further comprising, after aspirating a first portion, redirecting the aspiration cannula such that the cannula advances into the marrow cavity along a second path within the marrow cavity, where the second path is different from the first path.

22. The method of claim 15 wherein processing comprises intra-operatively enriching the stem cells.

23. The method of claim 15 wherein processing comprises post-operatively enriching the stem cells.

24. The method of claim 15 wherein processing comprises enriching hematopoietic or mesenchymal stem cells contained within the aspirated bone marrow.

25. The method of claim 15 wherein introducing comprises delivering the enriched stem cells into an infarcted or injured coronary tissue region.

* * * * *